United States Patent
Sliski et al.

(10) Patent No.: US 8,272,088 B2
(45) Date of Patent: Sep. 25, 2012

(54) PATIENT SUPPORT SYSTEM FOR FULL ACCESS PRONE POSITION BREAST RADIOTHERAPY

(75) Inventors: Alan P. Sliski, Lincoln, MA (US); Jason Koshnitsky, Framingham, MA (US)

(73) Assignee: Orbital Therapy LLC, Bedford, MA (US)

( * ) Notice: Subject to any disclaimer, the term of this patent is extended or adjusted under 35 U.S.C. 154(b) by 787 days.

(21) Appl. No.: 12/205,418

(22) Filed: Sep. 5, 2008

(65) Prior Publication Data
US 2009/0064413 A1    Mar. 12, 2009

Related U.S. Application Data

(60) Provisional application No. 60/970,288, filed on Sep. 6, 2007.

(51) Int. Cl.
*A61G 13/02* (2006.01)
(52) U.S. Cl. ............... 5/601; 378/209; 5/607; 5/611
(58) Field of Classification Search ............ 5/600, 601; 378/65, 68, 37, 203, 208, 209, 196–198; 600/429
See application file for complete search history.

(56) References Cited

U.S. PATENT DOCUMENTS

| | | | |
|---|---|---|---|
| 5,289,520 A | 2/1994 | Pellegrino et al. | |
| 5,564,438 A * | 10/1996 | Merchant | 5/613 |
| 6,325,538 B1 | 12/2001 | Heesch | |
| 6,448,571 B1 | 9/2002 | Goldstein | |
| 6,883,194 B2 * | 4/2005 | Corbeil et al. | 5/601 |
| 6,886,198 B2 * | 5/2005 | Marin et al. | 5/601 |
| 6,987,831 B2 * | 1/2006 | Ning | 378/37 |
| 7,076,821 B2 * | 7/2006 | de Mooy | 5/601 |
| 7,373,676 B2 * | 5/2008 | Markovic et al. | 5/601 |
| 7,526,066 B2 * | 4/2009 | Koshnitsky et al. | 378/68 |
| 7,758,241 B2 * | 7/2010 | Sliski et al. | 378/203 |
| 7,763,864 B2 * | 7/2010 | Formenti | 250/453.11 |
| 7,817,774 B2 * | 10/2010 | Partain et al. | 378/37 |
| 7,957,503 B2 * | 6/2011 | Kobayashi | 378/37 |
| 8,027,711 B2 * | 9/2011 | Jones et al. | 600/407 |
| 2002/0156365 A1 | 10/2002 | Tsekos | |
| 2004/0034932 A1 * | 2/2004 | Zacharopoulos et al. | 5/601 |
| 2004/0041107 A1 | 3/2004 | Cadwalader et al. | |
| 2004/0081273 A1 * | 4/2004 | Ning | 378/37 |

(Continued)

OTHER PUBLICATIONS

International Search Report dated Apr. 12, 2008, issued in corresponding International Application No. PCT/US2008/075421.

(Continued)

*Primary Examiner* — Robert G Santos
*Assistant Examiner* — Brittany Wilson
(74) *Attorney, Agent, or Firm* — Intrinsic Law Corp; Ibrahim M. Hallaj (57) ABSTRACT

A patient support system to be used in conjunction with a standard linear accelerator, and other sources, is described that allows access of the treatment beam to the breast from up to 360 degrees. This support system places the patient in a prone position with the breast going through an aperture. The prone position increases the separation of the breast from the chest wall and other critical organs and reduces motion of the target tissue due to breathing. This invention offers up to 360 degree radiation beam access to the breast. This helps in skin sparing, better dose conformity, and allows one to use modern treatment techniques such as IMRT and IGRT. It also includes a provision for an imaging system. This invention can also be used with CT and MR imaging modalities.

7 Claims, 12 Drawing Sheets

U.S. PATENT DOCUMENTS

| | | | |
|---|---|---|---|
| 2004/0088791 A1* | 5/2004 | Corbeil et al. | 5/601 |
| 2004/0103477 A1* | 6/2004 | Gagnon et al. | 5/601 |
| 2005/0005356 A1* | 1/2005 | Zacharopoulos et al. | 5/601 |
| 2005/0028279 A1* | 2/2005 | de Mooy | 5/601 |
| 2005/0218348 A1 | 10/2005 | Fehrenbacher et al. | |
| 2007/0018111 A1 | 1/2007 | Calderon et al. | |
| 2007/0033735 A1 | 2/2007 | Formenti | |
| 2007/0064867 A1* | 3/2007 | Hansen et al. | 378/37 |
| 2007/0206203 A1 | 9/2007 | Trainer | |
| 2007/0211854 A1 | 9/2007 | Koshnitsky et al. | |
| 2008/0201850 A1* | 8/2008 | Brito et al. | 5/601 |
| 2009/0110146 A1 | 4/2009 | Sliski et al. | |
| 2009/0232273 A1* | 9/2009 | Sendai | 378/20 |
| 2010/0074400 A1* | 3/2010 | Sendai | 378/37 |
| 2010/0080344 A1* | 4/2010 | Schilling et al. | 378/37 |
| 2010/0080349 A1* | 4/2010 | Kalender et al. | 378/37 |
| 2010/0246760 A1* | 9/2010 | Li et al. | 378/37 |
| 2011/0047702 A1* | 3/2011 | Diao | 5/601 |
| 2011/0200178 A1* | 8/2011 | Mansfield | 378/209 |

OTHER PUBLICATIONS

International Search Report dated Dec. 24, 2008, issued in corresponding International Application No. PCT/US2008/081329.

Goodman, Karyn A. et al., "Dosimetric Analysis of a Simplified Intensity Modulation Technique for Prone Breast Radiotherapy," Int. J. Radiation Oncology Biol. vol. 60, No. 1, pp. 95-102, 2004.

"Prone Breast System." Bionix Radiation Therapy. Jun. 12, 2009 <www.bionix.com/Images/ProneBreast.pdf>.

"Prone Breast Patient Positioning." CDR Systems. Jun. 12, 2009 <www.cdrsys.ca/breast/>.

"Horizon Prone Breastboard." Civco Medical Solutions. Jun. 12, 2009 <http://civco.com/oncology/bt-positioning/horizonprone/>.

* cited by examiner

PATIENT SUPPORT SYSTEM FOR FULL ACCESS PRONE POSITION BREAST RADIOTHERAPY

RELATED APPLICATIONS

This application claims the benefit of U.S. Provisional Application Ser. No. 60/970,288, filed Sep. 6, 2007, the contents of which are incorporated herein by reference, in their entirety.

BACKGROUND OF THE INVENTION

In order to treat cancer with radiation, it is highly desirable to maximize the dose delivered to the target volume containing the tumor which is visible with various imaging modalities and some predetermined margin while sparing normal tissue.

Many mechanical configurations of radiation therapy machines and the associated radiation sources have been developed since Roentgen discovered X-Rays. Modern radiation therapy systems use relatively high energy beams of radiation from radioactive isotopes, particle beam accelerators, or electron beam X-Ray generators. The X-Ray generators can employ either high voltage direct current or RF driven linear accelerators (LINACs). The conventional radiation therapy system uses a LINAC to generate an electron beam with between 4 and 22 MeV of energy at low current. The electron beam strikes a high-Z target, typically tungsten, and generates penetrating x-rays. The beam is shaped and delivered to the target volume from one or more directions. The overlapping dose at the target volume is usually higher than the dose at the surface from any one delivery angle. The skin is sensitive to radiation, so it is desirable to limit the skin dose to minimize complications. If more delivery angles are used, the surface dose can be spread out and minimized with respect to the dose delivered to the target volume. A significant fraction of all radiation therapy treatments are employed to treat breast cancer with very good success. A typical general purpose radiation therapy system is designed to treat virtually all anatomical sites with some trade-offs being made in the design in order to make a universally applicable machine. A linear accelerator rotates about a horizontal axis, around a virtual point called the isocenter that intersects with the beam axis. A typical source to axis distance, or source to isocenter distance, SAD is 100 centimeters. The treatment couch rotates about a vertical axis intersecting with the same isocenter and including three additional Cartesian motions for patient alignment. The external dimensions and geometry of different linear accelerators vary, resulting in different available treatment angles, which can be limiting to couch position and gantry rotation.

Currently most of the breast cancer patient population is treated in the supine (lying on the back) position, which does not allow access from more than a few angles. The supine position is also inferior due to gravitational forces compressing the breast against the chest. In addition, breast motion resulting from breathing creates inaccuracies in locating the beam with respect to the target volume.

Alternatively, a prone position radiation therapy is used for access to the breast. This method is implemented with a table top attachment that works with a standard linear accelerator. This embodiment helps to reduce target motion associated with breathing and create a better separation of the target tissue with respect to the chest wall and other critical structure. However, this embodiment still only allows access to a few angles, typically two.

SUMMARY OF THE INVENTION

This invention relates to a patient support system to be used with conventional radiation sources to position the patient in a more favorable geometry by allowing up to 360 degree access to the breast with the patient in the prone position.

This invention solves one of the remaining issues in breast cancer treatment, which is access to the breast from multiple angles, up to 360 degrees. The patient support system of the present invention can be made out of suitable materials making it CT and MR compatible for use with imaging modalities.

The present invention is directed to a prone position patient support system to be used in conjunction with a radiation source. The patient support system includes an anatomically contoured patient interface surface and an aperture to permit passage of the anatomy to be treated through the patient interface surface. The patient supports system further includes a support system for the patient interface surface that provides space below the patient interface surface to allow beam access from a radiation source for at least 180 degrees of rotation in a substantially horizontal plane.

In one embodiment, the radiation source is a LINAC. In another embodiment, the radiation source is a supervoltage x-ray generator. In another embodiment, the radiation source is a particle beam accelerator.

In one embodiment, the support system is CT compatible. In another embodiment, the patient support system is MR compatible.

In one embodiment, the support system further includes a rotational mechanism that allows rotation about the longitudinal axis of the patient support system.

In one embodiment, the support system includes one or more imaging components and associated software algorithms for patient registration.

In one embodiment, the support system for the patient interface surface further comprises a longitudinal translation stage and a rotary stage.

In one embodiment, the support system for the patient interface surface further comprises cross shaped radiolucent spacers for separating the patient interface surface and a bottom structure.

In accordance with another aspect of the invention, the invention is directed to a prone position patient support system to be used in conjunction with a radiation source. The patient support system includes an anatomically contoured patient interface surface and an aperture to permit passage of the anatomy to be treated through the patient interface surface. The patient support system further includes a support system for the patient interface surface that provides space below the patient interface surface to allow beam access from a radiation source for at least 270 degrees of rotation in a substantially horizontal plane.

In one embodiment, the radiation source is a LINAC. In another embodiment, the radiation source is a supervoltage x-ray generator. In another embodiment, the radiation source is a particle beam accelerator.

In one embodiment, the support system is CT compatible. In another embodiment, the support system is MR compatible.

In one embodiment, the support system includes one or more imaging components and associated software algorithms for patient registration.

In one embodiment, the support system for the patient interface surface is designed from radio-lucent material.

In one embodiment, the support system for the patient interface surface is geometrically designed such that the radiation beam is unobstructed.

In one embodiment, the support system includes a rotational mechanism that allows rotation about the longitudinal axis of the patient support system.

In one embodiment, the support system for the patient interface surface is geometrically designed to have limited interference with the radiation beam.

In one embodiment, the support system for the patient interface surface further comprises a longitudinal translation stage and a rotary stage.

In one embodiment, the support system for the patient interface surface further comprises cross shaped radiolucent spacers for separating the patient interface surface and a bottom structure.

In accordance with another aspect of the invention, the invention is directed to a prone position patient support system to be used in conjunction with a radiation source. The patient support system includes an anatomically contoured patient interface surface and an aperture to permit passage of the anatomy to be treated through the patient interface surface. The patient support system further includes a support system for the patient interface surface that provides space below the patient interface surface to allow beam access from a radiation source for 360 degrees of rotation in a substantially horizontal plane.

In one embodiment, the radiation source is a LINAC. In another embodiment, the radiation source is a supervoltage x-ray generator. In another embodiment, the radiation source is a particle beam accelerator.

In one embodiment, the support system is CT compatible. In another embodiment, the support system is MR compatible.

In one embodiment, the support system includes one or more imaging components and associated software algorithms for patient registration.

In one embodiment, the support system for the patient interface surface is designed from radio-lucent material.

In one embodiment, the support system for the patient interface surface is geometrically designed such that the radiation beam is unobstructed.

In one embodiment, the support system includes a rotational mechanism that allows rotation about the longitudinal axis of the patient support system.

In one embodiment, the support system for the patient interface surface further comprises a longitudinal translation stage and a rotary stage.

In one embodiment, the support system for the patient interface surface further comprises cross shaped radiolucent spacers for separating the patient interface surface and a bottom structure.

In accordance with another aspect of the invention, the invention is directed to a prone position patient support system to be used in conjunction with a radiation source. The patient support system includes a contoured patient support surface including an aperture to permit passage of the anatomy to be treated through the patient support surface and a lower support structure. The patient support system further includes a support member between the patient support surface and the lower support structure which provides space between the patient support surface and the lower support structure. The patient support system further includes a treatment couch on which the lower structure is coupled and the treatment couch has a rotary base. A rotational mechanism is coupled to the lower structure and the treatment couch which allows beam access from a radiation source for 360 degrees in a substantially horizontal plane.

In one embodiment, the radiation source is a LINAC. In another embodiment, the radiation source is a supervoltage x-ray generator. In another embodiment, the radiation source is a particle beam accelerator.

In one embodiment, the patient support system is CT compatible. In another embodiment, the patient support system is MR compatible.

In one embodiment, the rotational mechanism allows rotation about the longitudinal axis of the patient support system.

In one embodiment, the support system includes one or more imaging components and associated software algorithms for patient registration.

In one embodiment, the rotational mechanism comprises a longitudinal translation stage and a rotary stage.

In one embodiment, the support member comprises cross shaped radiolucent spacers for separating the patient interface surface and a bottom structure.

BRIEF DESCRIPTION OF THE DRAWINGS

The foregoing and other features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
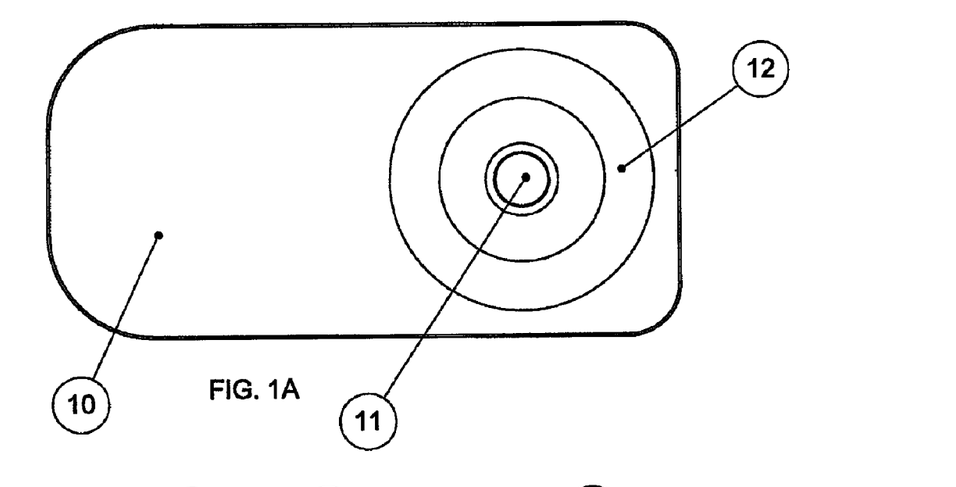
FIG. 1A is a top view of the patient support system that allows radiation beam access of less than 360 degrees as the support structure for the table top obscures beam access from a limited range of angles according to an embodiment of the present invention.
Figure 1B:
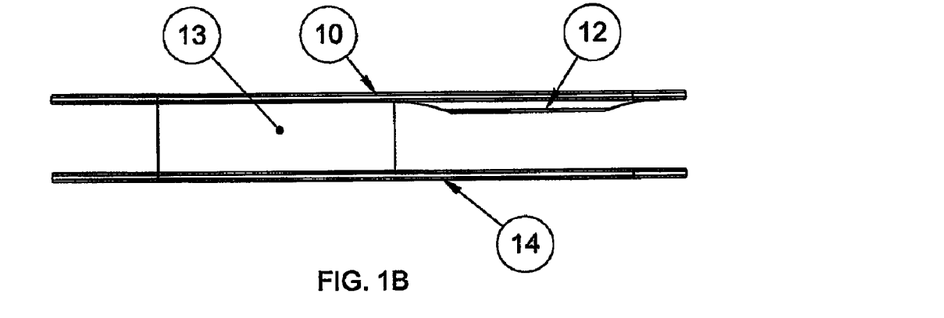
FIG. 1B is a side view of the patient support system shown in FIG. 1A that would be mounted on a conventional linear accelerator treatment couch.
Figure 1C:
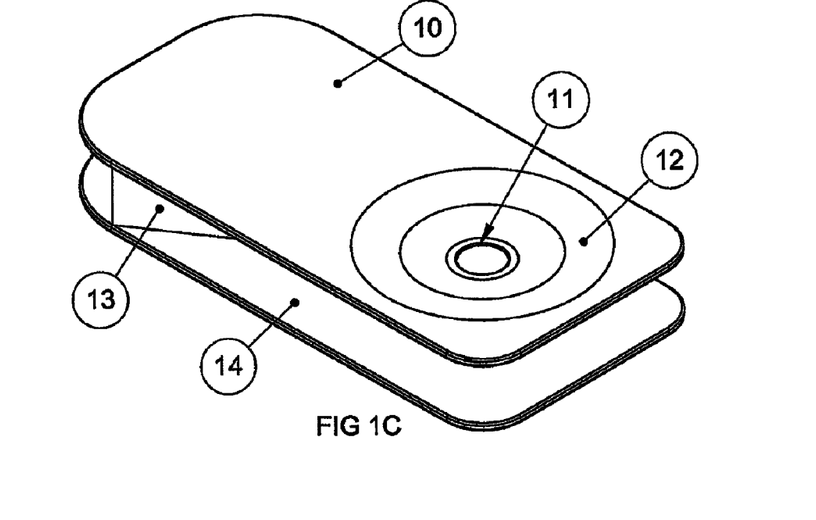
FIG. 1C is an isometric view of the patient support system shown in FIG. 1A.
Figures 7A, 7B, 7C:
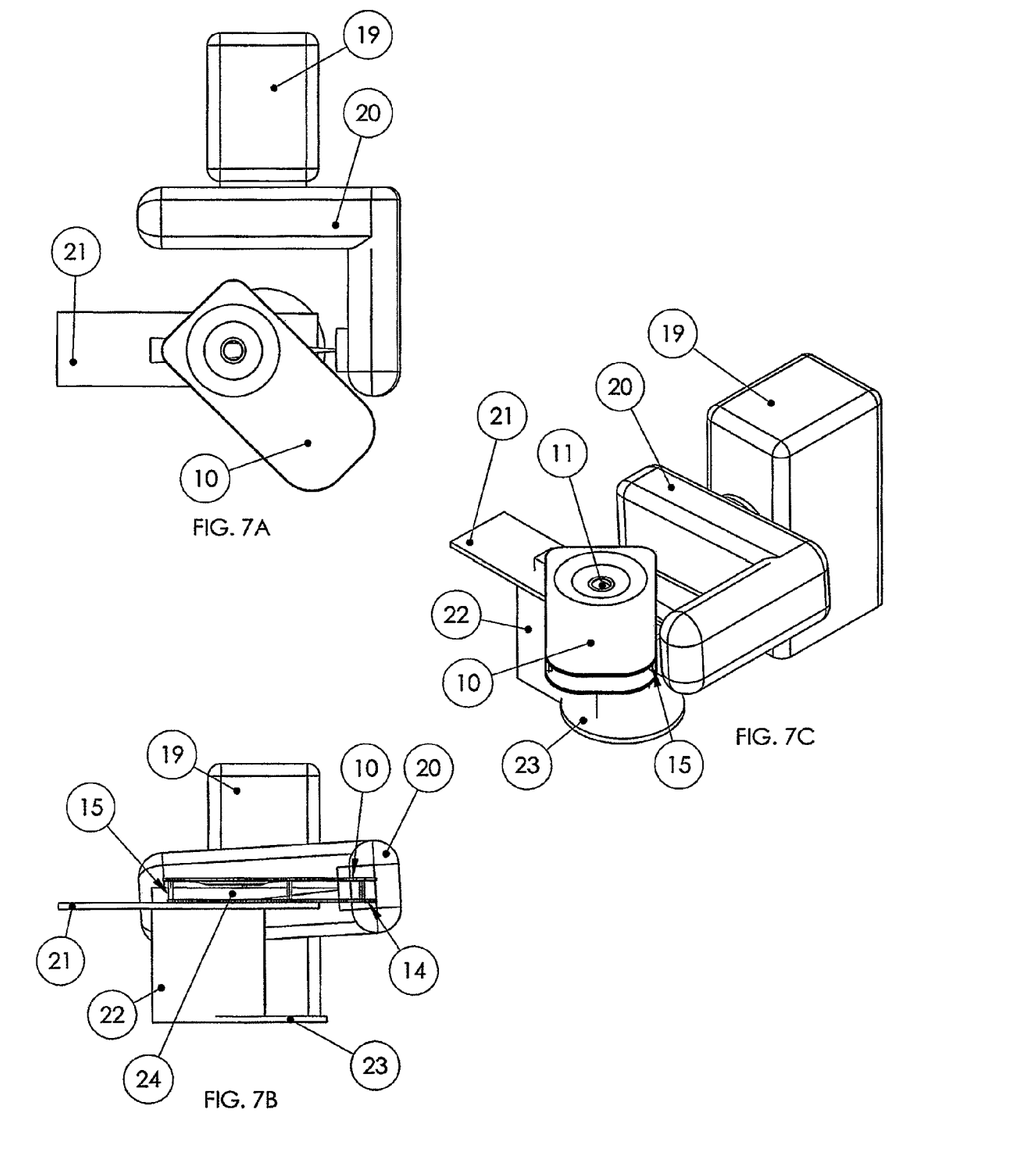

This invention combines a unique support system with novel geometric motions to allow access to treat the breast in the prone position from up to 360 degrees. Presently this range of access and motion is not possible with conventional LINAC couches or existing attachments. An anatomically designed patient support surface 10 with contour 12 provides a surface for the patient to lie on during positioning and treatment. The contour 12 of the support surface 10 combined with the shape and size of the aperture 11 allows the patient to lie comfortably in position during set-up and treatment while allowing the anatomical volume of interest to protrude through the aperture 11. A series of inserts of different size, shape, and symmetry (not shown) can be provided to allow small breasts to be treated comfortably in one extreme, while a large, asymmetrically shaped aperture can allow the chest wall and other related anatomy such as the axilla to be accessed for treatment. The support system can be made in mirror-image versions with left and right versions of the apertures for treating the left and right breast to maximize patient comfort and anatomy accessibility. Cushions can be provided for the support surface 10 and contour 12 to increase comfort during the procedure, which is typically 15 minutes with a beam-on time of 1 minute. The support surface 10 can be gently heated to increase patient comfort as well. A set of cushions that tilt the patient around the longitudinal axis can be provided to maximize access and comfort. The patient support system is shown in two basic configurations in FIGS. 1A-C and 2A-C as attachments. FIGS. 1A-C have a triangular shaped support member 13 between the upper support surface 10 and bottom structure 14. This provides unobstructed access to the breast over a wide range of angles, but not 360 degrees. This is a simple configuration that can be placed on an existing commercial LINAC treatment couch and provides much of the benefit of treating from a wide range of angles. As shown in FIG. 7A, because a treatment couch 21 and the patient support surface 10 interfere with the LINAC gantry 20, a full range of angles is not physically accessible. The triangular support member 13 does not limit access by the radiation beam to the breast over the range of physically possible angles for a given combination of LINAC and couch. The upper support surface 10 is made of a stiff, radiolucent material such as carbon fiber over a foam or honeycomb core, which has sufficient torsional and longitudinal stiffness to support the patient in a cantilevered configuration without significant deflection. In this configuration, the invention consists of a simple, light add-on attachment to an existing treatment system, but provides much of the advantage of the more integrated, complex implementations also described here and included in the overall invention.

Figure 2A:
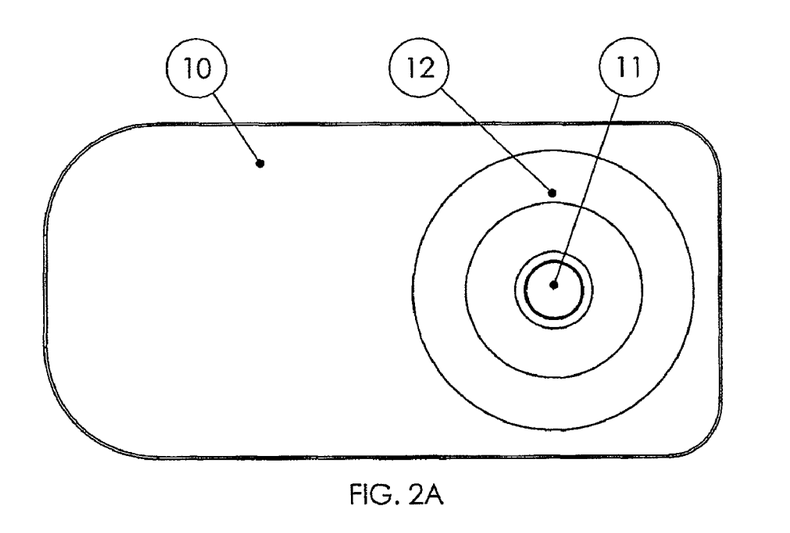
FIG. 2A is a top view of the patient support system of the present invention that allows radiation beam access up to 360 degrees by using non-shadowing supports according to an embodiment of the present invention.
Figure 2B:
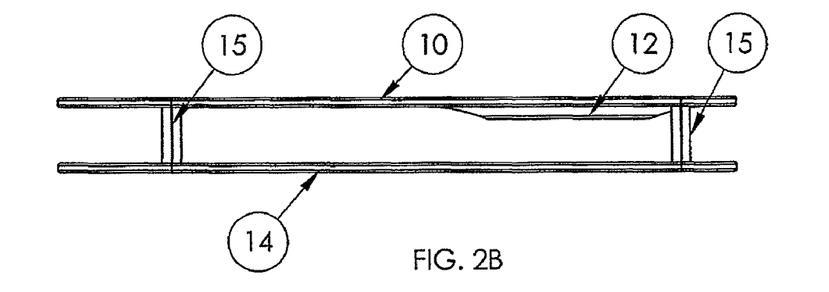
FIG. 2B is a side view of the patient support system shown in FIG. 2A.
Figure 2C:
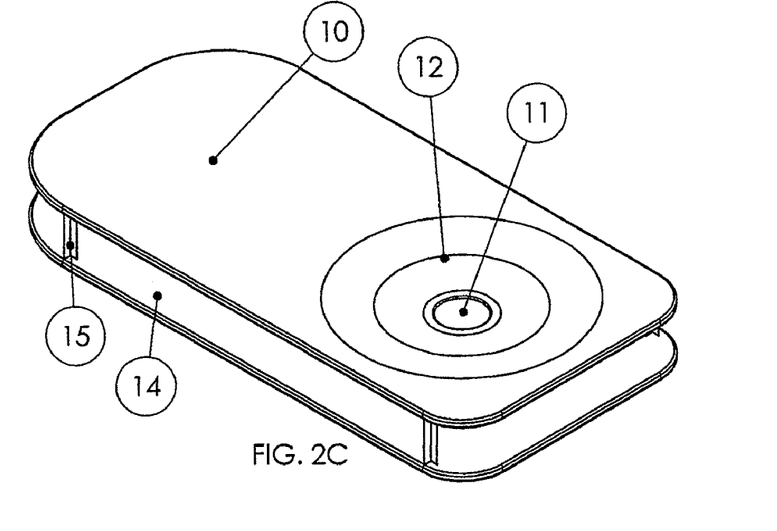
FIG. 2C is an isometric view of the patient support system shown in FIG. 2A.
Figure 3A:
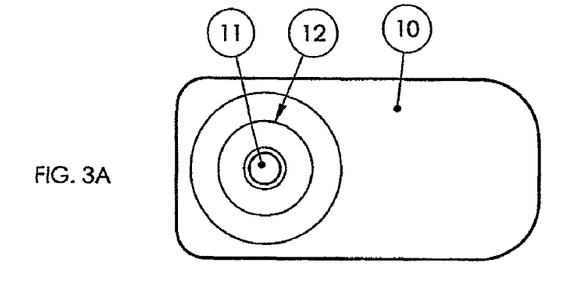
FIG. 3A is a top view of another embodiment of the patient support system that allows radiation beam access up to 360 degrees by using non-shadowing supports with an additional rotation stage and translation stage according to an embodiment of the present invention.
Figure 3B:
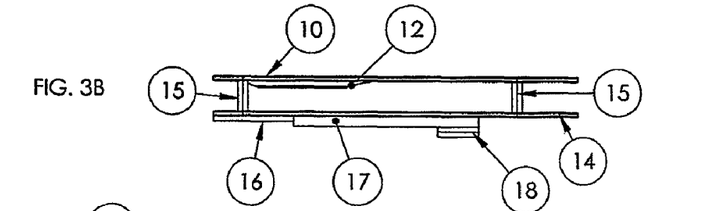
FIG. 3B is a side view of the patient support system shown in FIG. 3A.
Figure 3C:
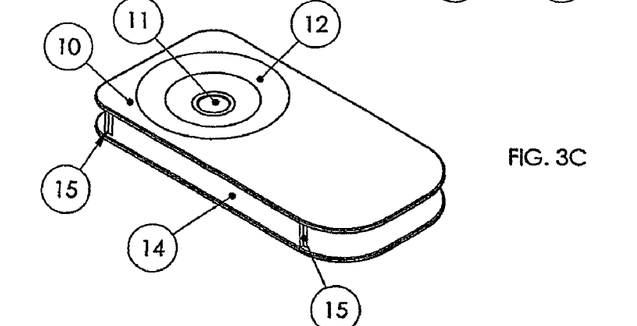
FIG. 3C is an isometric view of the patient support system shown in FIG. 3A.
Figure 3D:
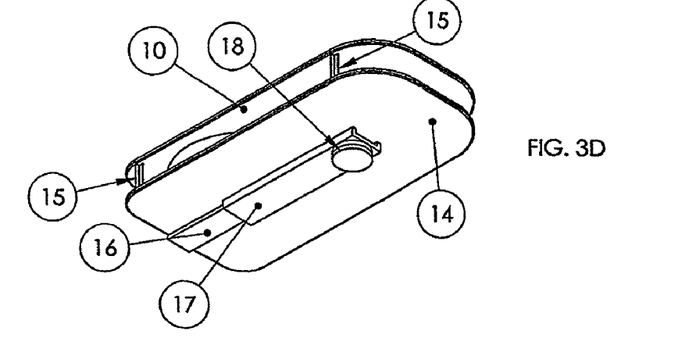
FIG. 3D is a bottom view of the patient support system shown in FIGS. 3A, 3B and 3C.

A second level of performance and complexity is shown in FIGS. 2A-C. A similar set of top patient support surface 10 and bottom structure 14 are separated by radiolucent spacers 15 with locations and orientations designed to minimize absorption of radiation. Radiolucent spacers 15 that are cross shaped are shown, and the orientation of the supports is such that radiation will not traverse the long axis of the material on its way to the breast at isocenter. The cross shaped radiolucent spacers 15 project about 2.8 times the thickness of the material into the path of the beam. If the beam traverses two adjacent sections of the support at 45 degrees, the total thickness seen by the beam is 2.8 times the thickness of the material. A square tube has similar characteristics, but a round tube creates shadows where the beam traverses the edges of the round tube tangentially. The support system or a similar one of the same geometry is used in a CT machine prior to treatment to obtain a set of images used for treatment planning. These images can be used to create a set of digitally reconstructed radiographs (DRRs) that can be used with an imaging system that is optionally part of this support system. These DRRs are used to compare the patient's position during set-up to insure correct positioning of the anatomy to be treated. The imaging system can consist of optical cameras mounted in one or more locations such as on the bottom of the bottom support structure 14, out of the path of the treatment beam, on the LINAC gantry 20, and on the walls of the room, mounted next to or coaxially with the alignment lasers typically installed in treatment rooms. The capability to acquire images, process the images and compare them to the treatment planning images is an optional part of this invention.

Figure 4A:
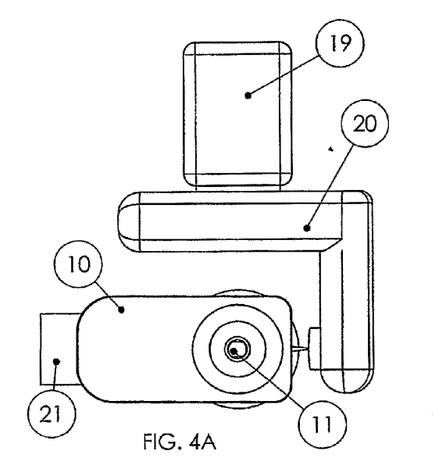
FIGS. 4A-C, 5A-C, 6A-C, 7A-C, 8A-C, 9A-C, 10A-C and 11A-C show top, side, and isometric views, respectively, of the variable patient support system technique that allows 360 degree access to the breast using the additional rotation and translation capability shown in FIGS. 3A-D.
Figure 4B:
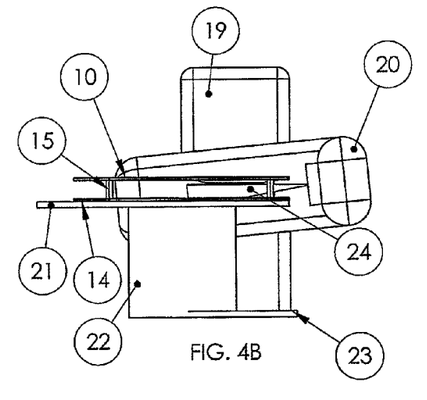
Figure 4C:
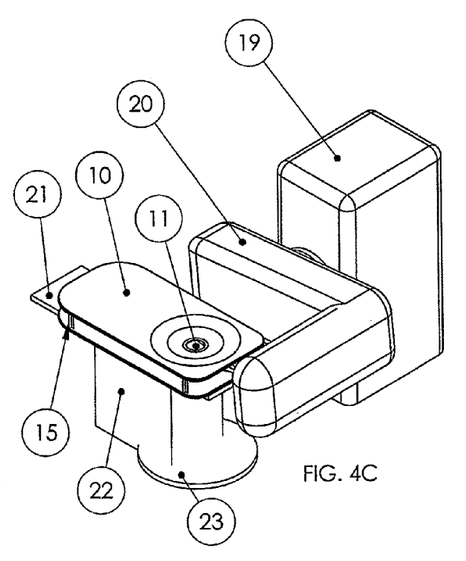
Figures 5A, 5B, 5C:
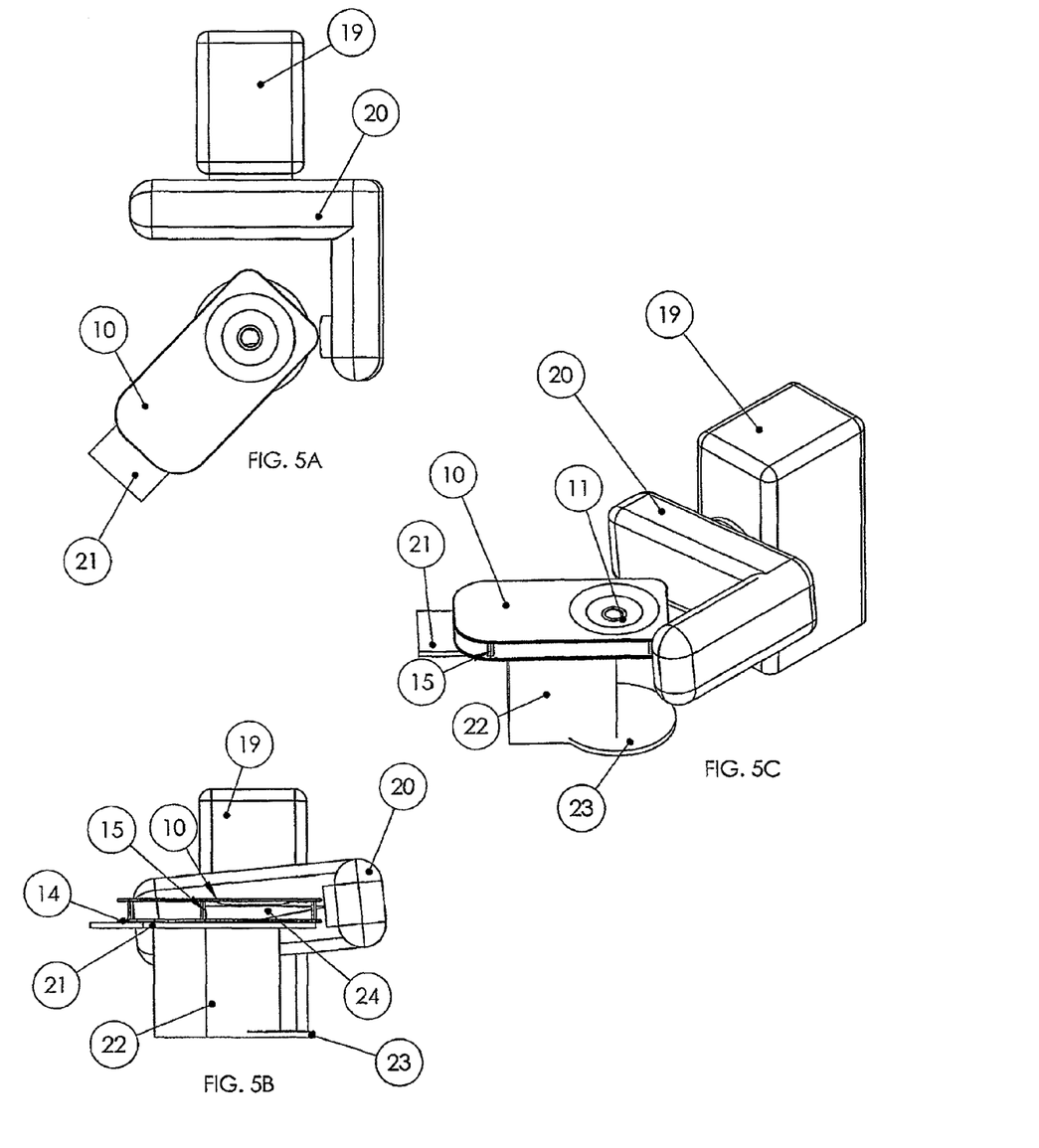
Figure 6A:
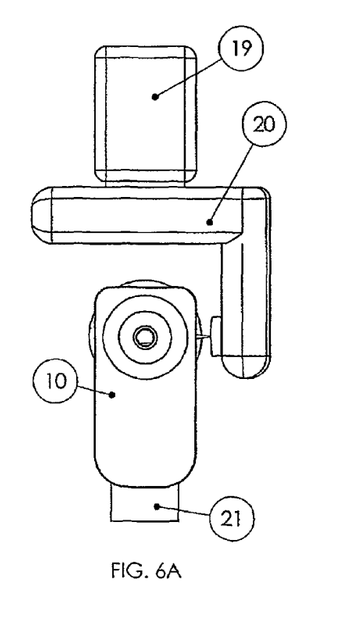
Figure 6B:
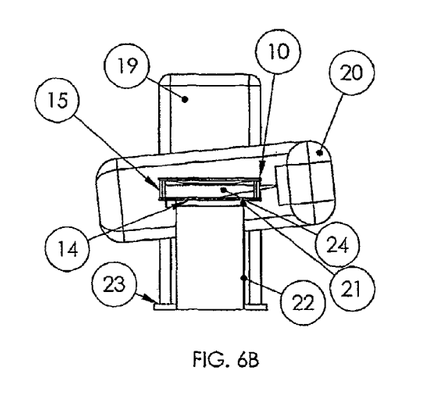
Figure 6C:
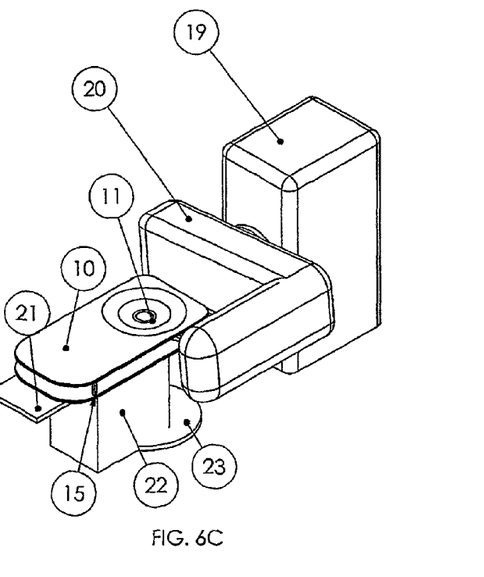
Figure 8A:
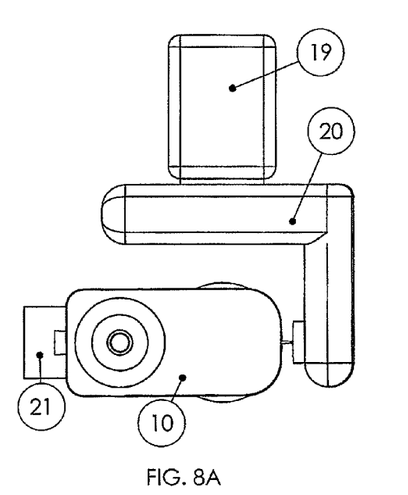
Figure 8B:
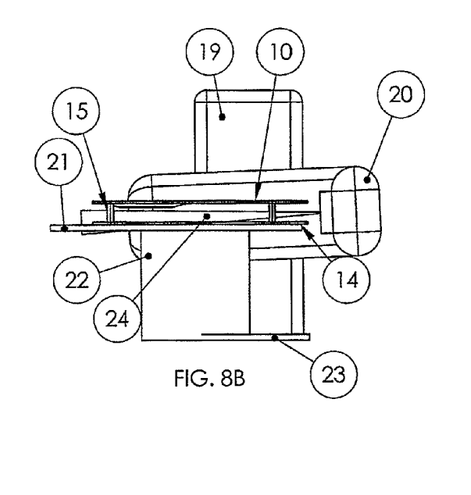
Figure 8C:
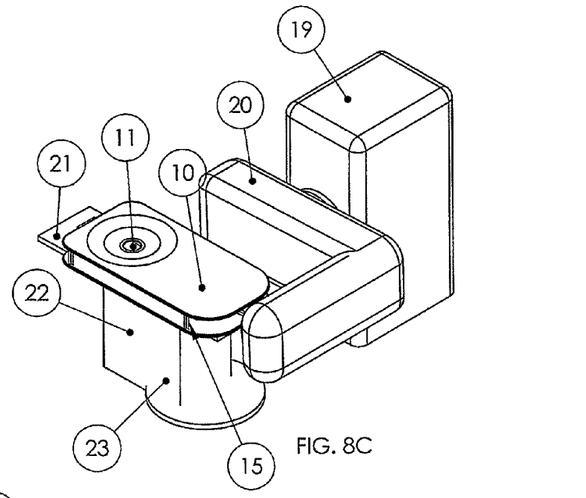
Figure 9A:
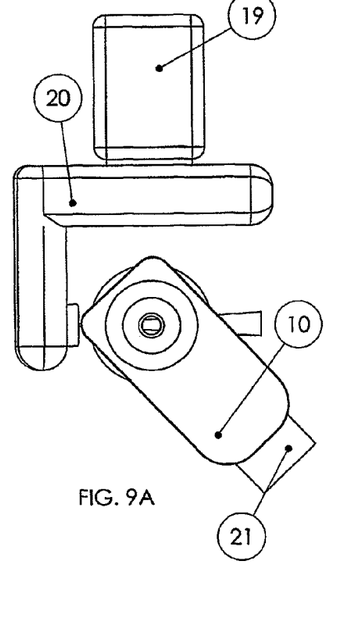
Figure 9B:
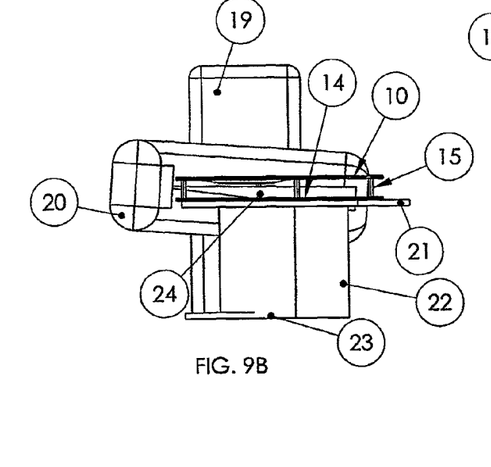
Figure 9C:
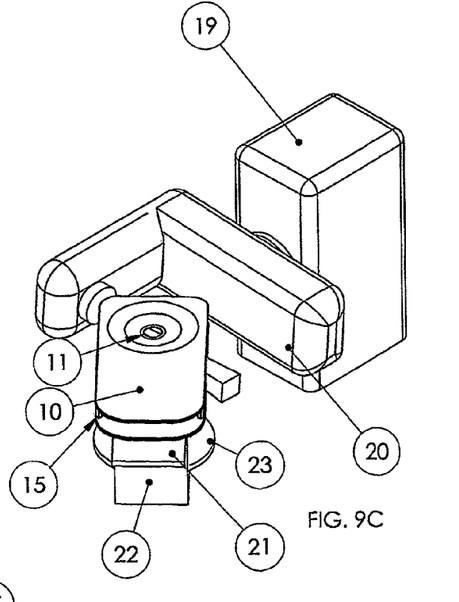
Figure 10A:
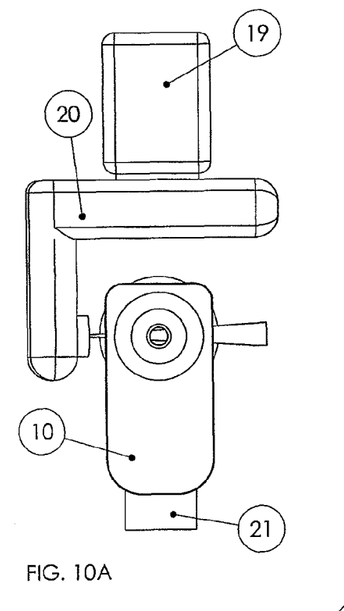
Figure 10B:
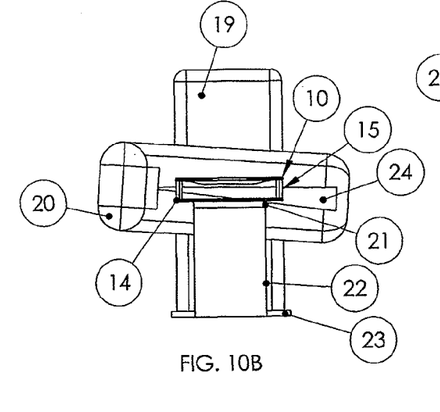
Figure 10C:
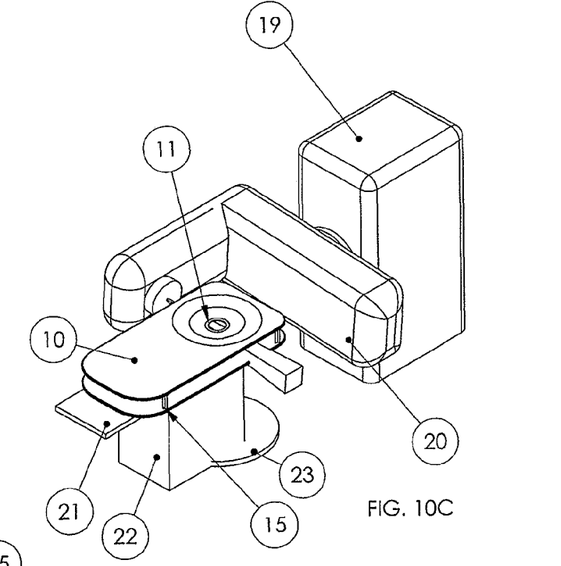
Figures 11A, 11B, 11C:
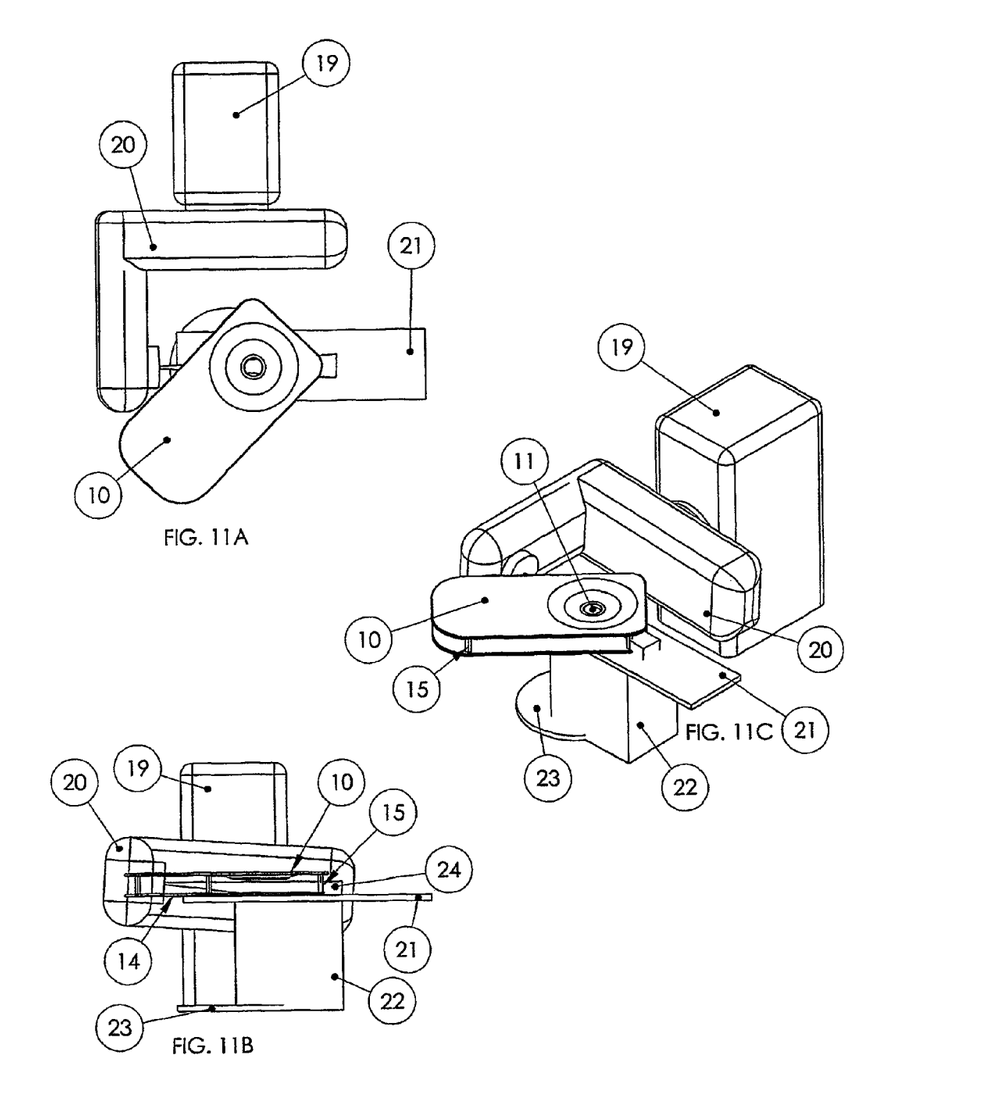
Figure 12A:
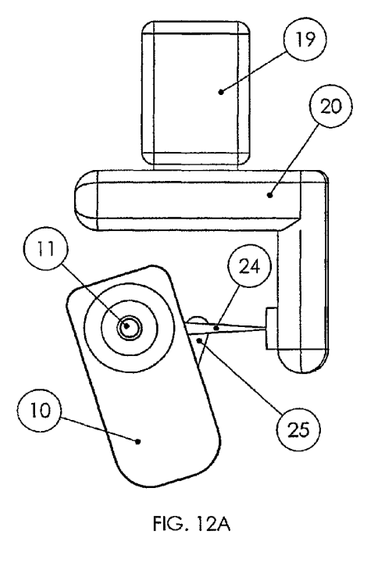
FIGS. 12A-D illustrate the patient support system of FIGS. 3A-D mounted on a jointed support in accordance with the present invention.
Figure 12B:
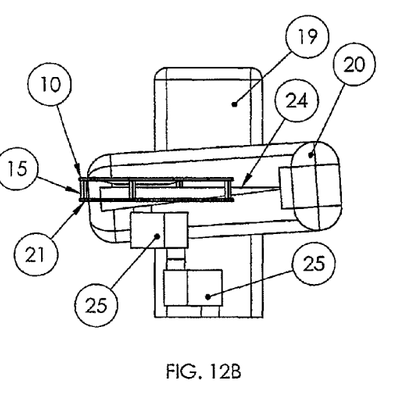
Figure 12C:
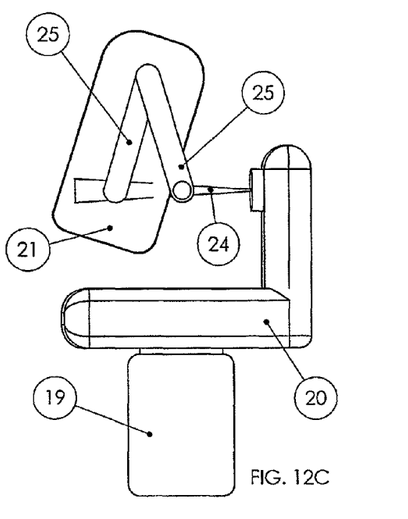
Figure 12D:
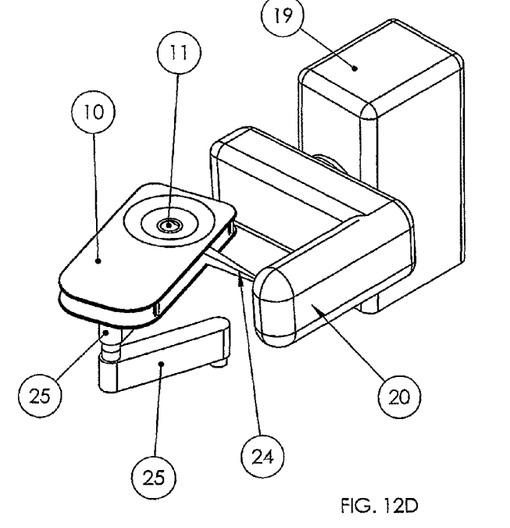

FIGS. 3A-D illustrate the support system with an additional longitudinal translation stage 16 and 17, as well as an additional rotary stage 18. The rotary stage 18 is fastened to the LINAC couch 21 of FIGS. 4A-C, 5A-C, 6A-C, 7A-C and 8A-C and these two additional degrees of freedom allow the support system to orient the breast for access to the treatment beam through a full range of 360 degrees. The translation stage 16 and 17 and the additional rotary stage 18 allow the support system to move in a longitudinal axis of patient support system. In the positions shown in FIGS. 7A-C, the support surface 10 would interfere with the LINAC gantry 20 if the support surface was not moved away from the LINAC treatment head using the translational stage 16 and 17 and rotary stage 18 shown in FIGS. 3B and 3D. In the position shown in FIGS. 8A-C, the distance from the patient's breast to the patient's feet is greater than the typical distance from the LINAC isocenter to the treatment head. It is necessary to use an increased SAD for large treatment angles. The range of positions and angles are shown in FIGS. 4A-C, 5A-C, 6A-C, 7A-C and 8A-C collectively. Treatment with increased SAD can be easily planned for once the geometrical limitations of the system are characterized. FIGS. 4A-C show the patient support system in position to provide treatment on a LINAC at an angle which is defined as 90 degrees. The patient support system is at an angle of zero degrees when the long axis of the treatment couch 21 is parallel to the rotational axis of LINAC gantry 20. The gantry 20 is rotated into a substantially horizontal position such that the upper surface of the radiation beam 24 is almost horizontal for this phase of treatment. All anatomy that projects through the aperture 11 can be treated in this configuration. Additional treatments can be delivered to related sites such as the axilla, in which there are lymph nodes that may contain cancer cells that have migrated from the primary tumor. These are located under the arm near the armpit and are treated with radiation if they are found to be positive for cancer cells upon biopsy.

FIGS. 4A, 5A, 6A, 7A and 8A illustrate plan views of different rotations of the support surface 10. FIGS. 4B, 5B, 6B, 7B and 8B illustrate side views of the corresponding conditions. FIGS. 4C, 5C, 6C, 7C and 8C illustrate isometric views of these configurations. FIGS. 4A-C, 5A-C, 6A-C, 7A-C and 8A-C illustrate the different rotational angles of the support surface 10. FIGS. 9A-C, 10A-C and 11A-C are mirror images of FIGS. 5A-C, 6A-C and 7A-C, respectively, which together in conjunction with rotating the LINAC gantry 20 describe 45 degree steps in a full 360 degree rotation to treat the breast from all angles. Any given treatment may include treatment from one or more angles, and the most advanced version of treatment where the beam is on continuously during patient rotation is also possible. FIGS. 4A-C, 5A-C, 6A-C and 7A-C further illustrate a LINAC cabinet 19, a treatment couch Z axis motion 22, a couch rotary base 23 and the radiation beam 24.

The support system can be made as an integral part of a custom couch instead of as an attachment. Increased flexibility is obtained by integrating the structures instead of making an add-on attachment. Better access to oblique angles departing from the substantially horizontal position is possible by eliminating duplicate structures and providing cut-outs in strategically located areas. A patient support system as described may additionally be mounted on a "frog-leg" jointed support or robotic arm 25 which increases performance and flexibility, as shown in FIGS. 12A-D. An additional rotational motion can be incorporated into the add-on or integrated versions to allow tilting the patient support surface along the longitudinal axis, thus allowing greater comfort for the patient and creating better positioning for the left and right breasts. Either version of this invention can be used with any radiation source including radioisotopes, LINACs, ortho- or super-voltage x-ray generators or particle beam accelerators.

The embodiments of the present invention can be used in conjunction with an already existing table, e.g., a treatment couch, or incorporated into the design of an entirely new treatment couch.

The patient support system of the present invention can be made out of materials making it CT and MR compatible for use with imaging modalities. The patient support system further includes one or more imaging components and associated software algorithms for patient registration.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A prone position patient support system for radiation therapy of a patient to be used in conjunction with a radiation source, comprising:
    an automatically contoured patient support surface;
    an aperture in the support surface to permit passage of the anatomy to be treated through the patient support surface aperture; and
    a support system for the patient support surface that provides space below the patient support surface to allow substantially unobstructed beam access from a radiation source for at least 180 degrees of rotation in a substantially horizontal plane, said support system further comprising a rotational mechanism that allows rotation about a longitudinal axis of the patient support system.

2. The patient support system of claim 1 wherein the support system is CT compatible.

3. The patient support system of claim 1 wherein the support system is MR compatible.

4. The patient support system of claim 1 further comprising one or more imaging components and associated software algorithms for patient registration.

5. The patient support system for claim 1 wherein the support system for the patient interface surface further comprises a longitudinal translation stage and a rotary stage.

6. The patient support system of claim 1 wherein the support system for the patient support surface further comprises radiolucent spacers for separating the patient interface surface and a bottom structure.

7. The patient support system of claim 1 wherein the support system is configured to support the patient support surface in a substantially cantilevered configuration.

* * * * *

UNITED STATES PATENT AND TRADEMARK OFFICE
CERTIFICATE OF CORRECTION

PATENT NO. : 8,272,088 B2
APPLICATION NO. : 12/205418
DATED : September 25, 2012
INVENTOR(S) : Alan P. Sliski and Jason Koshnitsky It is certified that error appears in the above-identified patent and that said Letters Patent is hereby corrected as shown below:

In the Claims

Column 8, line 7, Claim 1, "automatically" should be changed to --anatomically--.

Signed and Sealed this
Eighteenth Day of June, 2013

Teresa Stanek Rea
*Acting Director of the United States Patent and Trademark Office*